(12) United States Patent
Josse et al.

(10) Patent No.: US 7,875,034 B2
(45) Date of Patent: Jan. 25, 2011

(54) SPINAL DISC SPACE PREPARATION INSTRUMENTS AND METHODS FOR INTERBODY SPINAL IMPLANTS

(75) Inventors: Loic Josse, Denens (CH); Mingyan Liu, Bourg la Reine (FR); Jeffrey Zhang, Collierville, TN (US); Randy N. Allard, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 768 days.

(21) Appl. No.: 11/375,229

(22) Filed: Mar. 14, 2006

(65) Prior Publication Data
US 2007/0233143 A1 Oct. 4, 2007

(51) Int. Cl.
*A61B 17/58* (2006.01)
(52) U.S. Cl. .............. 606/90; 606/99; 606/914
(58) Field of Classification Search ........... 606/90, 606/99, 86 A, 100, 86 R, 914–915
See application file for complete search history.

(56) References Cited

U.S. PATENT DOCUMENTS

| | | | |
|---|---|---|---|
| 3,486,505 A * | 12/1969 | Morrison | 606/90 |
| 4,545,374 A | 10/1985 | Jacobson | |
| 4,697,586 A | 10/1987 | Gazale | |
| 5,059,194 A | 10/1991 | Michelson | |
| 5,122,130 A * | 6/1992 | Keller | 606/86 A |
| 5,135,528 A | 8/1992 | Winston | |
| 5,620,458 A | 4/1997 | Green et al. | |
| 5,722,977 A | 3/1998 | Wilhelmy | |
| 5,797,909 A | 8/1998 | Michelson | |
| 6,096,038 A | 8/2000 | Michelson | |
| 6,261,296 B1 | 7/2001 | Aebi et al. | |
| 6,270,498 B1 | 8/2001 | Michelson | |
| 6,277,149 B1 * | 8/2001 | Boyle et al. | 623/17.16 |
| 6,478,800 B1 | 11/2002 | Fraser et al. | |
| 6,530,955 B2 * | 3/2003 | Boyle et al. | 623/17.11 |
| 6,565,574 B2 | 5/2003 | Michelson | |
| 6,599,291 B1 | 7/2003 | Foley et al. | |
| 6,599,294 B2 | 7/2003 | Fuss et al. | |
| 6,755,841 B2 * | 6/2004 | Fraser et al. | 606/99 |
| 6,855,167 B2 * | 2/2005 | Shimp et al. | 623/17.11 |
| 2001/0031967 A1 | 10/2001 | Nicholson et al. | |
| 2002/0123754 A1* | 9/2002 | Holmes et al. | 606/105 |
| 2003/0149438 A1 | 8/2003 | Nichols et al. | |
| 2003/0171814 A1 | 9/2003 | Muhanna et al. | |
| 2003/0195517 A1 | 10/2003 | Michelson | |
| 2003/0233097 A1 | 12/2003 | Ferree | |
| 2004/0117022 A1 | 6/2004 | Marnay et al. | |
| 2004/0162562 A1 | 8/2004 | Martz | |
| 2004/0167536 A1 | 8/2004 | Errico et al. | |
| 2004/0176764 A1 | 9/2004 | Dant | |

(Continued)

FOREIGN PATENT DOCUMENTS

EP 0 676 176 A1 10/1995

(Continued)

*Primary Examiner*—Eduardo C Robert
*Assistant Examiner*—Jan Christopher Merene

(57) ABSTRACT

Instruments and methods for preparing a spinal disc space to receive an implant include an annulus template, a footprint template, a distractor for distracting adjacent vertebrae, and a guide member for guiding a chisel. The instruments and methods can be employed in an oblique approach to the spinal disc space.

14 Claims, 5 Drawing Sheets

U.S. PATENT DOCUMENTS

| | | |
|---|---|---|
| 2004/0176773 A1 | 9/2004 | Zubok et al. |
| 2004/0176777 A1 | 9/2004 | Zubok et al. |
| 2004/0176778 A1 | 9/2004 | Zubok et al. |
| 2004/0176848 A1 | 9/2004 | Zubok et al. |
| 2004/0199168 A1 | 10/2004 | Bertagnoli et al. |
| 2004/0215198 A1 | 10/2004 | Marnay et al. |
| 2004/0225295 A1 | 11/2004 | Zubok et al. |
| 2004/0225366 A1 | 11/2004 | Eisermann et al. |
| 2005/0010296 A1 | 1/2005 | Mitchell |
| 2005/0021042 A1 | 1/2005 | Marnay et al. |
| 2005/0027300 A1* | 2/2005 | Hawkins et al. ............ 606/86 |
| 2005/0055029 A1 | 3/2005 | Marik et al. |
| 2005/0113842 A1 | 5/2005 | Bertagnoli et al. |
| 2005/0165408 A1* | 7/2005 | Puno et al. .............. 606/99 |
| 2006/0195097 A1* | 8/2006 | Evans et al. ............. 606/61 |
| 2007/0123903 A1* | 5/2007 | Raymond et al. ......... 606/99 |
| 2007/0198016 A1* | 8/2007 | Zang et al. .............. 606/69 |

FOREIGN PATENT DOCUMENTS

| | | |
|---|---|---|
| EP | 0 681 811 A2 | 11/1995 |
| EP | 1 153 582 A2 | 11/2001 |

* cited by examiner

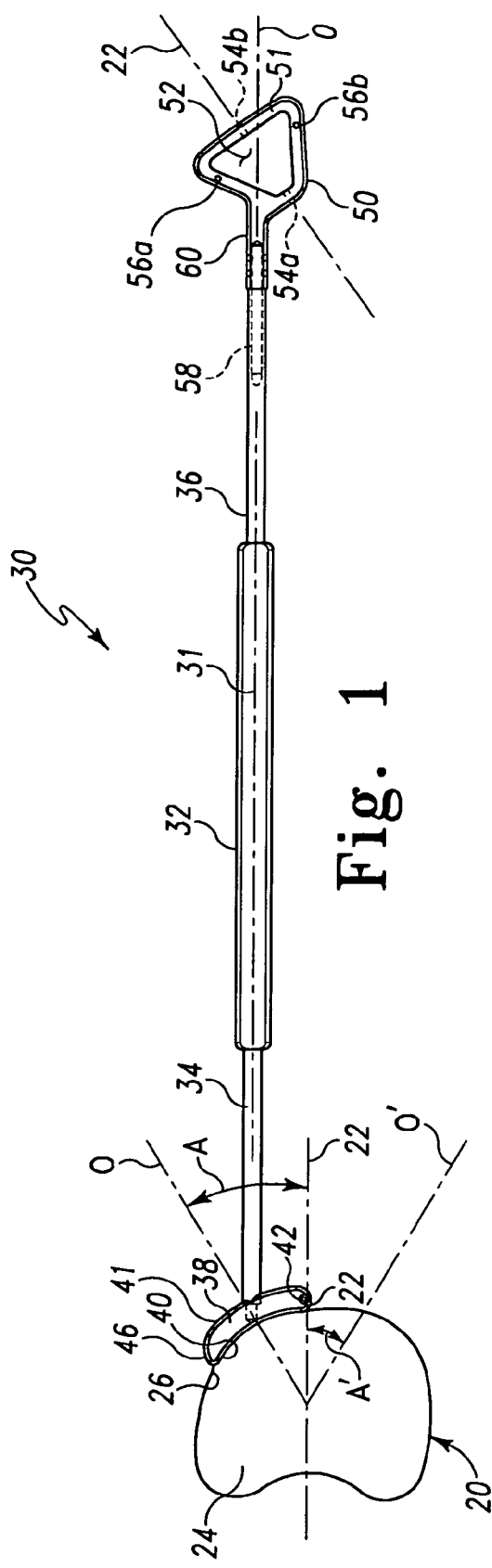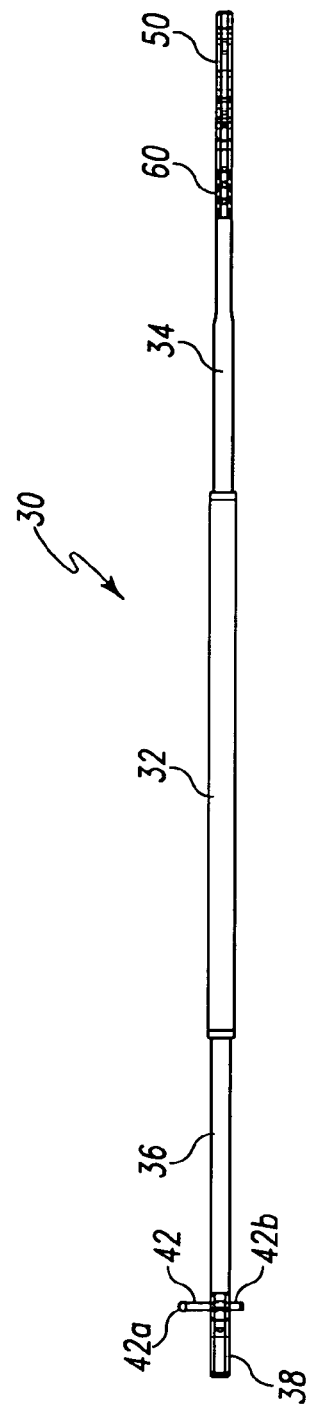

SPINAL DISC SPACE PREPARATION INSTRUMENTS AND METHODS FOR INTERBODY SPINAL IMPLANTS

BACKGROUND

Restoration and preparation of the space between vertebrae and preparation of the vertebral bodies can be important to obtain the desired fit of implants and other devices in the disc space and with the vertebral bodies. There remains a need for instruments and techniques that facilitate such restoration of the space between vertebrae and the preparation of the vertebrae to receive or engage implants.

SUMMARY

According to one aspect, there is provided an instrument positionable in a spinal disc space for distracting adjacent vertebrae. The instrument includes first and second plate portions positionable along an endplate of an adjacent vertebra. A shaft portion extends proximally from each of the plate portions to a hinge that connects the shaft portions to one another. The first and second plate portions further include opposite vertebral endplate contacting surfaces that define a distraction height therebetween. The instrument includes a handle at a proximal end of the shaft portions and a longitudinal passage between the handle and the plate portions. An actuating member in the passage includes an elongated shaft and an engaging member at a distal end of the shaft that is contactable with inner surfaces of the first and second plate portions. The actuating member and the engaging member are movable in the passage and the engaging member is structured to provide incremental adjustment of the distraction height between the vertebral endplate contacting surfaces based on a position of the engaging member relative to the inner surfaces of the first and second plate portions.

According to another aspect, an instrument is positionable in a spinal disc space for distracting adjacent vertebrae. The instrument includes first and second plate portions positionable along an endplate of an adjacent vertebra. A shaft portion extends proximally from each of the plate portions along a longitudinal axis to a hinge connecting the shaft portions to one another. The first and second plate portions further include opposite vertebral endplate contacting surfaces defining a distraction height therebetween. A handle is at a proximal end of the shaft portions. An actuating member is positionable in a passage extending between the handle and the plate portions. The actuator is operable to separate the first and second plate portions to increase the distraction height to distract the adjacent vertebrae. The plate portions further include a medial visualization marker adjacent a medial side thereof and a lateral visualization marker adjacent a lateral side thereof. The markers project from at least one of the first and second vertebral endplate contacting surfaces, and the medial marker is located distally of the lateral marker along the longitudinal axis. The markers are used to align the plate portions in the disc space since the markers align with one another in a lateral view of the adjacent vertebrae when the longitudinal axis is oriented along an oblique approach to the spinal disc space.

According to another aspect, an instrument assembly for preparing adjacent vertebrae includes a guide member and a chisel. The guide member includes a distal interbody member with opposite vertebral endplate contacting surfaces positionable in a disc space between the adjacent vertebrae. A shaft extends proximally from the guide member along a longitudinal axis and a handle member is at a proximal end of the shaft. A first elongated slot extends through the interbody portion and the shaft and a second elongated slot in communication with the first slot opens along one side of the handle. The chisel includes at least one blade positionable in the first slot with the at least one blade projecting therefrom. The chisel further includes an elongate shaft extending proximally from the at least one blade that is positionable through the side opening of the second slot to couple the chisel to the guide member.

According to yet another aspect, a templating instrument for spinal surgery includes an elongate handle with a first shaft portion extending in a first direction from the handle and a second shaft portion extending in a second direction from the handle opposite the first direction. An annulus template is located at an end of the first shaft portion opposite the handle. The annulus template includes a concavely curved distal end wall extending between a medial end and a lateral end. The distal end wall is positionable along an annulus extending between adjacent vertebrae with the lateral end offset in the first direction relative to the medial end. The templating instrument also includes a footprint template at an end of the second shaft portion opposite the handle. The footprint template is positionable in a spinal disc space between the adjacent vertebrae and is sized and shaped to provide an indication of an implant fit in the spinal disc space.

According to another aspect, a kit for preparing an intervertebral space to receive an interbody spinal implant from an oblique approach is provided. The kit includes a templating instrument, a distractor and a guide member for a chisel. The distraction and guide member are adapted for positioning in the spinal disc space along an oblique approach.

According to another aspect, a method for preparing an intervertebral space to receive an interbody implant includes: determining an annulus opening size to be made in an annulus with an annulus template along the annulus of the intervertebral space, the annulus template including a medial end alignable with a sagittal plane of the spinal column and a distal end wall extending from the medial end to a lateral end, the distal end wall including a size corresponding to the annulus opening size; making the opening in the annulus having the determined annulus opening size; incrementally distracting the intervertebral space to a desired disc space height with a distractor positioned through the opening along an oblique approach to the intervertebral space; and guiding a chisel into at least one vertebra adjacent the intervertebral space along a guide member, the guide member including an interbody member positioned in the intervertebral space and an elongated shaft extending proximally from the interbody member along the oblique approach.

These and other aspects are discussed below.

BRIEF DESCRIPTION OF THE DRAWINGS

FIG. 1 is a plan view of a templating instrument for an oblique approach to the spinal disc space and a diagrammatic plan view of a vertebra adjacent one end of the templating instrument.

FIG. 2 is an elevation view of the templating instrument of FIG. 1.

DESCRIPTION OF THE ILLUSTRATED EMBODIMENTS

Figure 3:
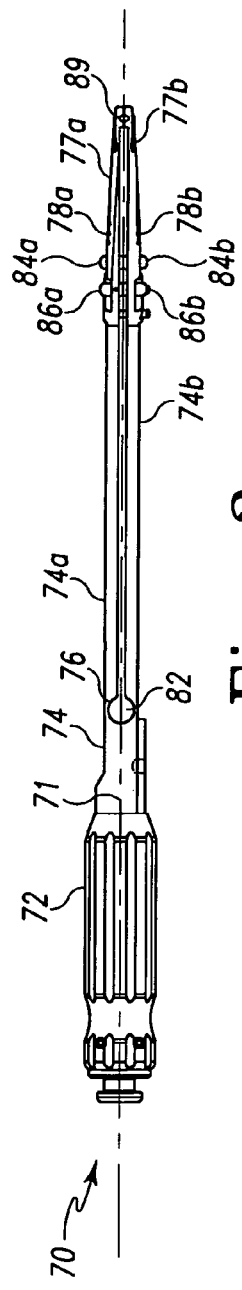
FIG. 3 is a side view of a distractor for insertion into a spinal disc space to distract adjacent vertebrae.

For the purposes of promoting an understanding of the principles of the present invention, reference will now be made to the embodiments illustrated in the drawings and specific language will be used to describe the same. It will nevertheless be understood that no limitation on the scope of the present invention is intended, and any alterations or modifications in the disclosed embodiments and further applications of the principles of the present invention are contemplated as would normally occur to one skilled in the art to which the present invention relates.

Instruments and methods are provided that indicate an appropriately sized and located opening and implant for positioning through the opening into an intervertebral space in an oblique approach to the spinal column. Instruments and methods are further provided for distracting the adjacent vertebrae and restoring the disc space between the adjacent vertebrae to a desired height to receive an implant from the oblique approach. Instruments and methods are further provided for guiding one or more chisels along an oblique path to prepare one or more vertebrae to receive a portion of the implant.

As used herein, an oblique approach is an approach that is non-parallel and non-orthogonal to the sagittal plane of the spinal column. While it contemplated that the oblique approach be taken anteriorly, applications with posterior-oblique approaches are contemplated. Furthermore, applications in anterior, posterior and lateral approaches to the spinal column that are not obliquely oriented are also contemplated.

The instruments can be provided in a kit alone or in combination with a spinal implant. In one form, the spinal implant is an artificial disc implant that includes one or more movable components to maintain or restore segmental motion, although other types of interbody implants are contemplated, including fusion devices. In a further form, the implant is adapted for insertion anteriorly in an oblique approach into the spinal disc space. Examples of such implants and others are provided in U.S. Patent Application Publication No. 2004/0225366, published on Nov. 11, 2004, which is incorporated herein by reference in its entirety. The instruments can be adapted to prepare the disc space and vertebrae to receive such an implant from the anterior oblique approach. Further examples of instruments and methods for preparing an intervertebral space to receive implants are also disclosed in U.S. Patent Application Publication No. 2005/0113842 published on May 26, 2005, which is also incorporated herein by reference in its entirety.

Referring to FIGS. 1 and 2, there is shown a templating instrument 30 for determining an appropriately sized and positioned opening through an annulus for an oblique approach to the spinal disc space 24 adjacent vertebra 20. Templating instrument 30 can further be employed for the dual function of determining the appropriately sized and shaped footprint of the implant to be implanted in spinal disc space 24. Templating instrument 30 includes an elongated handle portion 32 extending along a longitudinal axis 31. Handle portion 32 includes a first shaft portion 34 extending longitudinally in a first direction therefrom and a second shaft portion 36 extending longitudinally in a second direction therefrom opposite the first direction. Handle portion 32 can include a non-circular cross-section to facilitate gripping and manipulation of instrument 30 by the surgeon or other attendant.

First shaft portion 34 includes an annulus template 38 at an end thereof that is positionable along the annulus of disc space 24. Template 38 includes a banana-like shape with a concave distal end wall 40 and an opposite convex wall 41. Walls 40, 41 extend between a medial end 44 and a lateral end 46. Medial end 44 is positionable in alignment with the sagittal plane with concave wall 40 positioned against the annulus. Concave wall 40 extends laterally along the annulus to lateral end 46. In the operative position shown in FIG. 1, handle member 32 and shaft portion 34 are oriented so that longitudinal axis 31 extends generally parallel to and along the sagittal plane 22.

An indicator pin 42 is provided adjacent medial end 44 that is alignable with sagittal plane 22. Indicator pin 42 includes an upper portion 42a and a lower portion 42b abuttable against the adjacent vertebrae to facilitate positioning of annulus template 38 in the appropriate position along the annulus 26. Annulus template 38 provides a footprint along the annulus to indicate the extent of annulus removal that is desired to accommodate preparation of the vertebral space and insertion of the implant along an oblique approach O. Annulus template 38 can be removable from shaft portion 34 so that if lateral end 46 is positioned too far laterally or too far medially, a smaller or larger annulus template can be selected and attached to shaft portion 34 for measurement of another sized annulus footprint. Annulus template 38 can be engaged to shaft portion 34 by any suitable means, including a friction fit, projection-detent arrangements, collars, clamps, fasteners, or threaded engagement, for example.

Second shaft portion 36 includes a footprint template 50 sized and shaped to correspond to the size and shape, in plan view, of the footprint of the implant to be positioned in the spinal disc space. Footprint template 50 includes a wall 51 extending about a central space 52. Central space 52 provides a visual window to facilitate checking of the vertebral endplates relative to template 50. Footprint template 50 further includes anterior-posterior visualization markers 54a, 54b and medial-lateral visualization markers 56a, 56b. When footprint template 50 is properly positioned in the disc space, anterior-posterior markers 54a, 54b are aligned along the sagittal plane, and medial-lateral markers 54a, 54b are aligned with one another in the medial-lateral direction in or parallel to the coronal plane. A lateral image of the template 50 can be taken to adjust and/or confirm alignment of markers 56a, 56b in the disc space. In one embodiment, markers 54a, 54b, 56a, 56b are stainless steel or made from other suitable material viewable with an imaging system. Wall 51 can be made from a plastic or other translucent material to allow visualization of the disc space and the markers when footprint template 50 is positioned in the disc space. As used herein, the visualization markers are intended to include any type of marker made from any type of material that is viewable with any type of imaging system, including x-ray, fluoroscopic, CT scan, endoscopic, microscopic, loupes, and naked-eye imaging systems.

Footprint template 50 can be removably engaged to second shaft portion 36 so that if the attached footprint template does not indicate the proper or desired implant size for the disc space, a template of another size and/or shape can be attached to second shaft portion 36 and inserted into the spinal disc space. In the illustrated embodiment, footprint template 50 includes an extension 60 having a hollow tubular form to receive pin 58 extending from second shaft portion 36. Extension 60 can include projections or detents that receive correspondingly sized and shaped detents or projections of pin 58 to provide a positive engagement therewith. Other engagement means are also contemplated, including fasteners, friction fit, clamps, collars, threaded engagement, and spring-loaded mechanisms, for example.

Footprint template 50 is used by aligning axis 31 along the desired oblique approach O to the disc space 24. In one embodiment, oblique approach O forms an angle A with the sagittal plane 22. In one particular embodiment, angle A is about 35 degrees. In a further embodiment, angle A can range from 15 degrees to 45 degrees. Other embodiments contemplate angle A ranging from 0 degrees to 90 degrees. Footprint template 50 is inserted so that marker 54a is aligned along sagittal plane 22 in the anterior portion of the disc space and marker 54b is aligned along the sagittal plane in the posterior portion of the disc space. The apex of the triangularly-shaped footprint template 50 is positioned anteriorly and the base opposite the apex is positioned posteriorly. Medial-lateral markers 56a, 56b are aligned in the medial-lateral direction in the disc space, and are provided in the portions of wall 51 extending between the apex and the base portion. Other embodiments contemplate other shapes for footprint template 50 including rectangular, square, circular, oval, elliptical, banana, kidney, polygonal, and irregular shapes, for example. Furthermore, templates 38, 50 can be utilized in either the left side (patient's left) oblique approach O or the right side (patient's right) oblique approach O' oriented at angle A' by simply rotating template instrument 30 one hundred and eighty degrees about its longitudinal axis.

Figure 4:
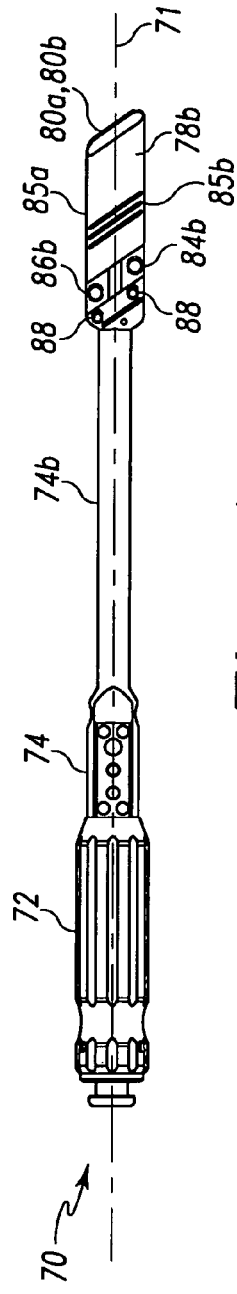
FIG. 4 is a plan view of the distractor of FIG. 3.
Figure 5:
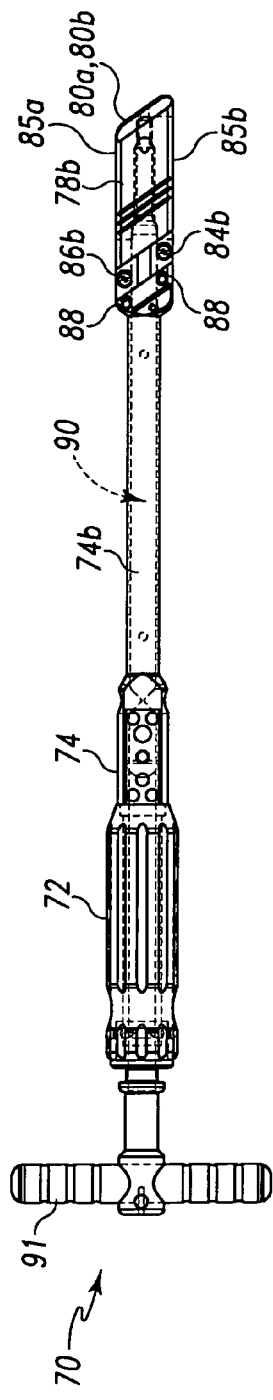
FIG. 5 is a plan view of the distractor of FIG. 4 with a handle member attached to an actuating member of the distractor.

FIGS. 3-5 show a distractor 70 positionable into disc space 24 along oblique axis O or O'. Distractor 70 includes a proximal handle 72 and a shaft 74 extending longitudinally from handle 72 along a longitudinal axis 71. Shaft 74 includes first and second elongated shaft portions 74a, 74b coupled to one another about a living hinge 76. Portions 74a, 74b are movable relative to one another about hinge 76. Each of the shaft portions 74a, 74b includes a plate portion 78a, 78b, respectively, extending from a distal end thereof. Alignment pins 88 extend from one of the plate portions 78a, 78b, to the other of the plate portions 78a, 78b adjacent the proximal ends of plate portions 78a, 78b. Alignment pins 88 are spaced from one another on opposite sides of longitudinal axis 71. At least one of the plate portions 78a, 78b is movable along alignment pins 88 as the plate portions 78a, 78b move toward and away from one another. Alignment pins 88 maintain plate portions 78a, 78b in alignment with one another and resist plate portions 78a, 78b from twisting and/or rotating relative to one another.

Plate portions 78a, 78b include opposite planar vertebral endplate contacting surfaces 77a, 77b to provide a broader surface area for contacting an adjacent vertebral endplate to distribute distraction forces thereto. Each of the plate portions 78a, 78b includes a distal end wall 80a, 80b, respectively, that is angled relative to longitudinal axis 71. The angled distal end walls 80a, 80b form a short side 85a of the plate portions 78a, 78b that is positioned laterally in the disc space and a long side 85b that is positioned medially in the disc space when shaft 74 is oriented along on of the corresponding oblique approaches O or O'. The angled end walls 80a, 80b and sides 85a, 85b of differing lengths allow end walls 80a, 80b to be substantially orthogonally oriented to sagittal plane 22 at the posterior edge or rim of the adjacent vertebral endplates of disc space 24 when axus 71 is oriented along the oblique axis O or O'.

Handle 72 and shaft 74 define a passage 82 extending therethrough that opens at the proximal end of handle 72. Passage 82 extends into the space between plate portions 78a, 78b. Plate portions 78a, 78b further include housings with medial markers 84 and lateral markers 86. Medial markers 84 include a first medial marker 84a projecting from first plate portion 78a and a second medial marker 84b projecting from second plate portion 78b adjacent medial side 85b. Similarly, lateral markers 86 include a first lateral marker 86a projecting from first plate portion 78a and a second lateral marker 86b projecting from second plate portion 78b adjacent lateral side 85a. An end opening 89 in communication with passage 82 can be provided in distal end walls 80a, 80b to allow visualization through distractor 70

Markers 84, 86 provide an indication to the surgeon when the desired angular and rotational alignment of plate portions 78a, 78b is achieved in the spinal disc space 24. The distractor is positioned so that when viewing a lateral x-ray or image, the first markers 84a, 86a are aligned with one another and the second markers 84b, 86b are aligned with one another so that only one superior and one inferior marker is visible in the image. In one embodiment, the markers include stainless steel balls captured in plastic housings extending from the plate portions 78a, 78b. Other embodiments contemplate other materials for the markers and housings that allow visualization and alignment of the distractor in the desired orientation relative to the spinal disc space.

Figure 7:
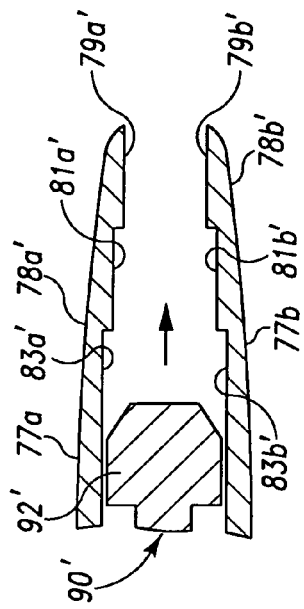
FIG. 7 is a sectional view along a distal portion of another embodiment distractor and actuating member therein.
Figure 6:
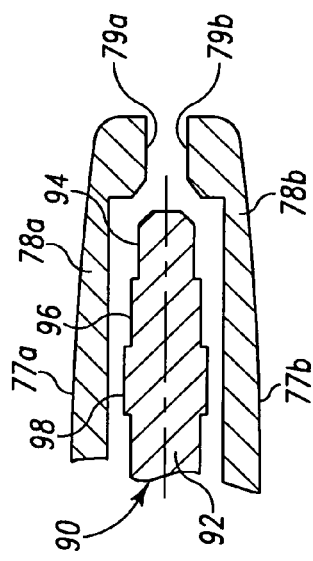
FIG. 6 is a sectional view along a distal portion of one embodiment distractor and actuating member therein.

In order to separate plate portions 78a, 78b to distract the vertebrae and provide a desired spacing between the endplates to receive the implant, an actuating mechanism is positionable in passage 82 and into contact with the inner surfaces of plate portions 78a, 78b, as shown in FIGS. 6 and 7. Actuating mechanism 90 includes a proximal handle member 91 (FIG. 5) and a distal engaging member 92 (FIG. 6). In FIG. 6, engaging member 92 includes a stepped configuration with first distal portion 94 having a first height, a second intermediate portion 96 having a second height greater than the first height, and a third proximal portion 98 having a third height greater than the second height. Plate portions 78a, 78b include inner surfaces 79a, 79b, respectively, that are engageable with engagement member 92.

When first portion 94 contacts inner surfaces 79a, 79b, a first distraction height for plate portions 78a, 78b is provided. Vertebral endplate contacting surfaces 77a, 77b are forced apart and into contact with the adjacent vertebral endplates to provide distraction. If additional distraction is desired, actuating member 90 can be advanced distally in passage 82 to contact second portion 96 with inner surfaces 79a, 79b. The edges leading into the space occupied by inner surfaces 79a, 79b can be beveled to facilitate movement of engaging member 92 therein. If further distraction is desired, actuating member 90 can be advanced further distally in passage 82 to contact third portion 98 with inner surfaces 79a, 79b.

In one specific example, first portion 94 can separate vertebral endplate contacting surfaces 77a, 77b to provide 8 millimeters distraction, second portion 96 can provide 10 millimeters distraction, and third portion 98 can provide 12 millimeters distraction. If more than 12 millimeters distraction is desired, a second actuating member can be provided with an engaging member that provides greater distraction heights therealong. The first actuating member can be withdrawn from passage 82 to accommodate insertion of the second actuating member. Alternatively or additionally, the actuating members can be provided with more than three distraction height increments, or less than three distraction height increments, including a single distraction height. Engaging members with portions providing distraction heights in increments other than two millimeters are also contemplated.

FIG. 7 shows an alternative arrangement where actuating member 90' includes an engaging member 92' of uniform height therealong. The inner surfaces of plate portions 78a', 78b' include a stepped configuration therealong that provide differing distraction heights depending on the stepped surface portion in which engaging member 92' is positioned into contact. For example, proximal stepped inner surface portions 83a', 83b' provide plate portions 78a', 78b' with a first distraction height between their vertebral endplate contacting surfaces 77a, 77b when engaging member 92' is in contact with inner surface portions 83a', 83b'. If additional distraction is desired, engaging member 92' is advanced distally into contact with intermediate stepped inner surface portions 81a', 81b' to provide a second distraction height greater than the first distraction height. If additional distraction is desired, then engaging member 92' is advanced into contact with the distal stepped inner surface portions 79a', 79b' to provide a third distraction height greater than the second distraction height. The leading distal end of engaging member 92' can be beveled to facilitate its advancement along the stepped surface portions.

Figure 8:
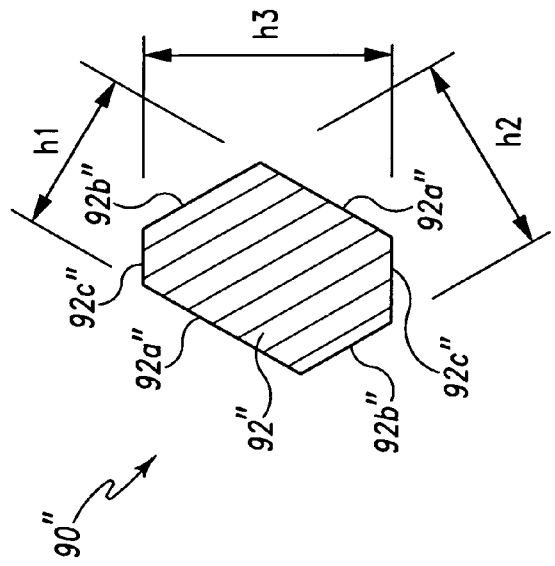
FIG. 8 is a section view across a distal portion of another embodiment actuating member for use with a distractor.
Figure 9:
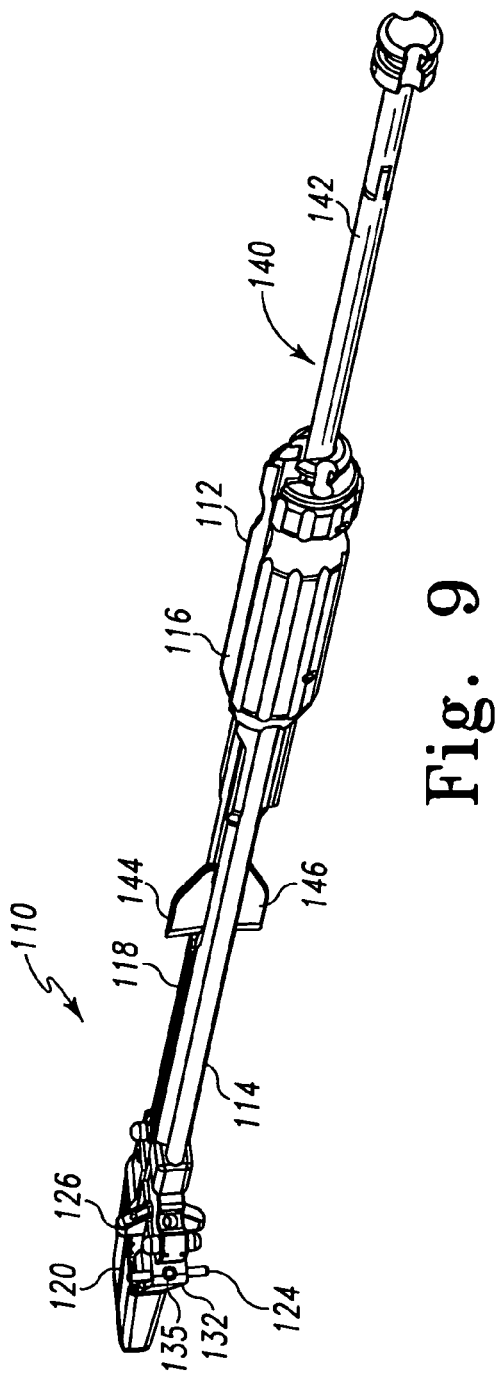
FIG. 9 is a perspective view of a chisel and guide member for the same for forming implant receiving areas in vertebrae to receive an implant from an oblique approach to a spinal disc space.
Figure 10:
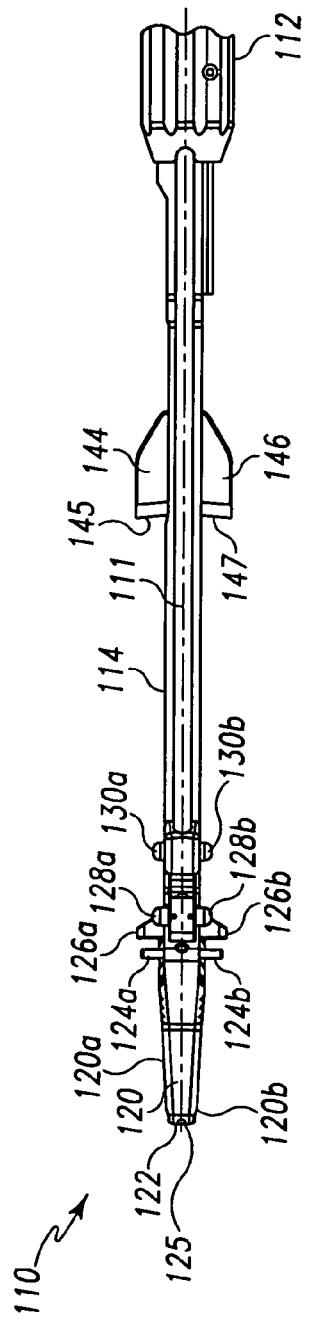
FIG. 10 is an elevation view of a portion of the chisel and guide member of FIG. 9.
Figure 11:
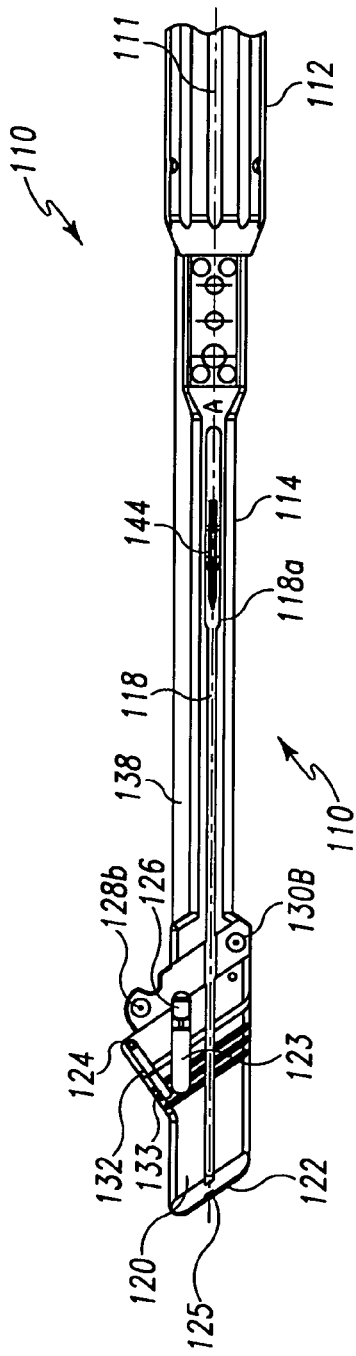
FIG. 11 is a plan view of a portion of the chisel and guide member of FIG. 9.
Figure 12:
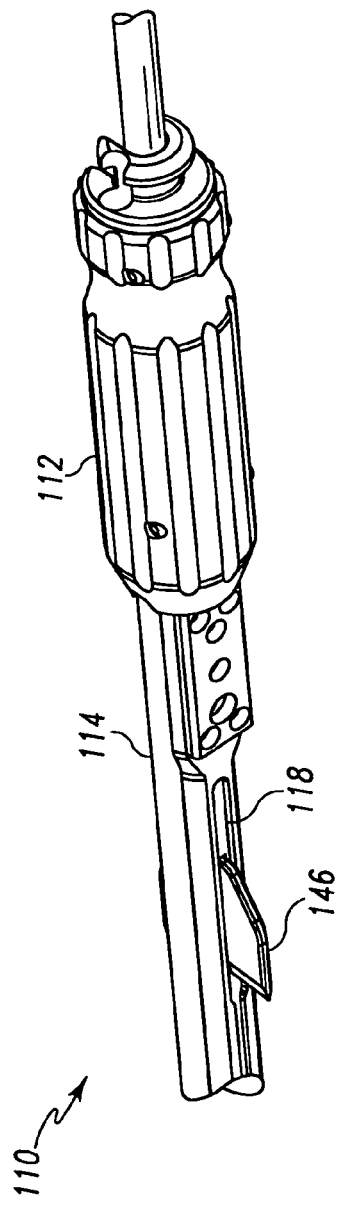
FIG. 12 is a perspective view of a portion of the chisel and guide member of FIG. 11.

In FIG. 8 there is shown another embodiment actuating mechanism 90" that is rotated between opposite cam surfaces to provide various distraction heights. As the various opposite cam surfaces contact the inner surfaces 79a, 79b of the plate portions 78a, 78b, differing separation distances are created to provide various distraction heights for vertebral endplate contacting surfaces 77a, 77b. For example, cam surface pairs 92a" provide a first, initial distraction height h1 when positioned into contact with inner surfaces 79a, 79b of plate portions 78a, 78b. If additional distraction is desired, actuating member 90" can be rotated in passage 82 with handle 91 to place second cam surface pairs 92b" in contact with inner surfaces 79a, 79b of plate portions 78a, 78b to provide a second, intermediate distraction height h2. Similarly, rotation of engaging member 92" so that third cam surface pairs 92c" contact inner surfaces 79a, 79b provides a third, intermediate distraction height h3.

The actuating member 90 can be provided with indicia readily observable to indicate the distraction height between the vertebral endplate contacting surfaces of the plate portions. Actuating member 90 can be coupled to handle 72 and/or shaft 74 with a threaded coupling arrangement so that rotation of handle 91 provides a mechanical advantage to axially translate actuating member 90 in passage 82 to provide the desired disc space distraction. Alternatively, the rotational forces applied to handle 91 can cause rotation of the engaging member about the axis of the actuating member, as would be desired for the embodiment of FIG. 8, to provide the desired distraction. In still another embodiment, impaction or axial forces can be applied to handle member 91 to axially translate actuating member 90 in passage 82 to provide the desired distraction.

After distraction of the disc space 24 has been obtained, distractor 70 can be removed and a guide member 110 can be positioned into disc space 24 along the same oblique approach employed with distractor 70. Guide member 110 is shown in FIGS. 9-12. Guide member 110 includes a proximal handle 112 and an elongate shaft 114 extending axially and distally from handle 112 along longitudinal axis 111. Handle 112 includes an elongate, side-opening slot 116 extending therealong to accept a shaft 142 of chisel 140. Shaft 114 further includes opposite elongate through-opening slot 118 through which chisel blades 144, 146 of chisel 140 project.

Guide member 110 includes an interbody member 120 at a distal end of shaft 114. Interbody member 120 includes a height between first and second endplate contacting surfaces 120a, 120b that corresponds to the distraction height achieved with distractor 70. Accordingly, the kit can be provided with a number of guides having interbody members with differing heights that correspond to distracted disc space heights. Slot 118 extends through interbody member 120 but is closed adjacent to distal end wall 122 to prevent displacement of the chisel blades 144, 146 therethrough. Distal end wall 122 can be obliquely angled relative to longitudinal axis 111 to allow positioning of interbody member 120 into the disc space in an orientation that mimics the orientation of first and second plate portions 78a, 78b of distractor 70.

Interbody member 120 includes a medial wing 132 with a midline indicator pin 124 extending therefrom. Pin 124 includes a first portion 124a and a second portion 124b projecting therefrom the contact the adjacent vertebral bodies when positioned thereagainst. Pin 124 is received in elongate slot 133, and can be moved therealong with an adjustment mechanism 135 to provide the desired positioning of pin 124 relative to interbody member 120. Indicator pin 124 can be aligned with the sagittal plane when interbody member 120 is in the disc space to provide an indication of the appropriate positioning of interbody member 120 therein.

To further assist in determining the proper orientation and placement of interbody member 120 in the disc space, interbody member 120 includes medial markers 128 and lateral markers 130. Medial markers 128 include a first medial marker 128a projecting from first endplate contacting surface 120a and a second medial marker 128b projecting from second endplate contacting surface 120b. Similarly, lateral markers 130 include a first lateral marker 130a projecting from first endplate contacting surface 120a and a second lateral marker 130b projecting from second endplate contacting surface 120b.

Markers 128, 130 provide an indication to the surgeon when the desired angular and rotational alignment of interbody member 120 is achieved in the spinal disc space 24. The interbody member 120 is positioned so that when viewing a lateral x-ray or image, the first markers 128a, 130a are aligned with one another and the second markers 128b, 130b are aligned with one another. In one embodiment, the markers are configured the same as those discussed above for distractor 70. In addition, a hole 125 in distal end wall 122 along axis 111 is provided. Endwall 122 and hole 125 are structured to be viewable in the lateral x-ray or image when interbody member 120 is properly oriented in the disc space.

Guide member 10 further includes a depth stop 126 to limit the insertion depth of interbody member 120 into the spinal disc space. Depth stop 126 includes first and second portions 126a, 126b that contact the adjacent vertebrae to prevent over insertion of interbody member 120 into the disc space. The depth of allowable insertion into the disc space can be adjusted by moving depth stop 126 proximally and distally in slotted hole 123. A shaft 138 extends from depth stop 126 and is threadingly engaged thereto. Rotation of shaft 138 causes depth stop 126 to move along slotted hole 123.

In use, interbody member 120 is positioned into the disc space along the oblique approach O or O' in which distractor 70 was positioned. Chisel 140 is loaded with shaft 142 received in slot 116 and blades 144, 146 into proximal portion 118a of slot 118. Proximal portion 118a can be enlarged relative to the distal portion of slot 118 to facilitate placement of blades 144, 146 therein. Furthermore, a key member between blades 144, 146 can be provided that is received in a keyway along slot 118 to maintain alignment of the blades 144, 146 relative to guide member 110. Blades 144, 146 are advanced distally along slot 118 until blades 144, 146 contact the respective vertebrae. Blades 144, 146 are then driven into the vertebrae in order to form slots in the vertebrae. Blades 144, 146 can include a distal cutting end 145, 147 for penetrating the vertebral body and forming a vertically oriented slot in the vertebral body as chisel blades 144, 146 are advanced therein. Other embodiments contemplate other forms for chisel 140, including a single blade or multiple blades along one side or along both sides for cutting multiple locations in the corresponding vertebrae, for example.

An impaction tool such as a slap hammer or mallet can tap the proximal end of shaft 142 to facilitate application of sufficient force to advance the blades into the vertebral bodies. Advancement is continued until blades 144, 146 contact the distal end of slot 118. The blades can then be withdrawn from the vertebrae, and interbody member 120 removed from the disc space. An implant can be positioned into the distracted disc space with engaging members, such as keels or other projections, being received in the slots formed into the vertebral bodies with the chisel blades.

For distractor 70 and guide member 110, the vertebral endplate contacting surfaces of plate portion 79a, 79b and interbody member 120 can include transverse recesses to engage the vertebral endplates and resist movement or migration of the plate portions/interbody member in the disc space. Other anti-migration structures are also contemplated, including surface roughenings, spikes, knurlings, and etchings for example. Smooth vertebral endplate contacting surfaces are also contemplated.

The vertebral endplate contacting surfaces of plate portions 79a, 79b and/or interbody member 120 can be tapered relative to one another such that the degree of angular separation between the surfaces decreases towards the distal ends. The taper angle defined between the vertebral endplate contacting surfaces can correspond to the particular lordotic angle desired between the endplates of the vertebrae on each side of the intervertebral disc space, and may take on any number of specific values, including 6 degrees, 9 degrees, and 12 degrees, for example. It should be understood, however, that other angles are contemplated, including angles at or near 0 degrees where the vertebral endplate contacting surfaces are arranged substantially parallel to one another.

The instruments herein can be provided in a kit with various surgical cutting instruments to prepare the adjacent vertebrae for insertion of a spinal implant therebetween. In such applications, the kit can include a guide member that functions as a jig or guide for surgical instruments that serve to cut, shave, bore, or otherwise prepare the vertebral endplates and/or disc space for insertion and engagement of an implant. An example of one such instrument is a chisel configured to cut a vertical slot into the vertebrae along the oblique approach. The oblique slot can accept a keel or extensions from the implant to assist in anchoring the implant in position in the intervertebral space.

The oblique approach that can be employed with the instruments herein allows the great vessels and other anatomical structures along the anterior of the spinal column to be avoided. The kit can allow the lateral surgical exposure during the preparation of the disc space and vertebral bodies to be maintained at exactly or nearly exactly the width of the prosthesis being implanted. It is to be understood a wide variety of uses for the instruments are contemplated. The instruments may be employed for disc space distraction and vertebral body preparation for insertion of one or more fusion cages, artificial discs, bone spacers, or other devices positionable in the spinal disc space. The instruments can be adapted for use in any approach to the disc space, including anterior, lateral, anterior-oblique, postero-lateral, and transforaminal approaches. The instruments can be employed together in a kit, or separately with other instruments.

While the invention has been illustrated and described in detail in the drawings and foregoing description, the same is to be considered illustrative and not restrictive in character. All changes, equivalents, and modifications that come within the scope of the invention described herein are desired to be protected.

What is claimed is:

1. An instrument positionable in a spinal disc space for distracting adjacent vertebrae, comprising:
    a first plate portion positionable along an endplate of one of the adjacent vertebrae;
    a second plate portion positionable along an endplate of the other of the adjacent vertebrae, said first and second plate portions each including a shaft portion extending proximally therefrom along a longitudinal axis to a hinge connecting said shaft portions to one another, said first and second plate portions further including opposite vertebral endplate contacting surfaces defining a distraction height therebetween, each of said first and second plate portions including a distal end and a proximally facing edge located proximally of said distal end of said respective plate portion, each of said edges extending from said respective plate portion toward the other of said first and second plate portions, said edges defining an entry into a space between said first and second plate portions with said first and second plate portions each including an inner surface extending along said space from said edge thereof to said distal end thereof;
    a handle at a proximal end of said shaft portions, said handle and said shaft portions defining a longitudinal passage; and
    an actuating member positioned in said passage, said actuating member including an elongated shaft and an engaging member at a distal end of said shaft in contact with said inner surfaces of said first and second plate portions, wherein said actuating member is movable in said passage to move said engaging member past said edges to contact said engaging member with said inner surfaces of said of said plate members so that said engaging member increases a spacing between said plate members based on a position of said engaging member in contact with said inner surfaces of said first and second plate portions, wherein said engaging member includes a stepped configuration along an outer surface thereof, said stepped configuration including a distal portion providing a first distraction height when contacting said inner surfaces of said first and second plate portions, an intermediate portion providing a second distraction height when contacting said inner surfaces of said first and second plate portions, and a proximal portion providing a third distraction height when contacting said inner surfaces of said first and second plate portions.

2. The instrument of claim 1, wherein said second distraction height is two millimeters greater than said first distraction height and said third distraction height is two millimeters greater than said second distraction height.

3. The instrument of claim 1, further comprising a medial visualization marker adjacent a medial side of said first and second plate portions and a lateral visualization marker adjacent a lateral side of said first and second plate portions each projecting from at least one said first and second vertebral endplate contacting surfaces, said medial marker being located distally of said lateral marker, wherein said medial and lateral markers are configured so that in a lateral image of the adjacent vertebrae said medial and lateral markers are aligned with one another so that only one of the medial and lateral markers is visible when said longitudinal axis is oriented along an oblique approach to the spinal disc space.

4. The instrument of claim 3, wherein said medial and lateral markers project from each of said first and second vertebral endplate contacting surfaces.

5. The instrument of claim 4, wherein said medial and lateral visualization markers each include a housing extending from said plate portion.

6. The instrument of claim 5, wherein each of said housings is plastic and each of said medial and lateral visualization markers is a metal ball captured in said housing.

7. The instrument of claim 1, wherein said hinge is an integral hinge at proximal ends of said first and second shaft portions.

8. The instrument of claim 1, wherein said first and second plate portions each include a distal end wall obliquely oriented with said longitudinal axis across said longitudinal axis, said first and second plate portions each including a proximal end and opposite sides extending between said distal end wall and said proximal end, wherein one of said opposite sides is longer than the other of said opposite side from said proximal end to said distal end wall.

9. An instrument positionable in a spinal disc space for distracting adjacent vertebrae, comprising:
a first plate portion positionable along an endplate of one of the adjacent vertebrae;
a second plate portion positionable along an endplate of the other of the adjacent vertebrae, said first and second plate portions each including a shaft portion extending proximally therefrom along a longitudinal axis to a hinge connecting said shaft portions to one another, said first and second plate portions further including opposite vertebral endplate contacting surfaces defining a distraction height therebetween, wherein said first plate portion and said second plate portion extend distally from said shaft portion along said longitudinal axis;
a handle at a proximal end of said shaft portions, said handle and said shaft portions defining a longitudinal passage;
an actuating member positionable in said passage operable to separate said first and second plate to increase the distraction height to distract the adjacent vertebrae; and
a medial visualization marker adjacent a medial side of said first and second plate portions and a lateral visualization marker adjacent a lateral side of said first and second plate portions each projecting from at least one said first and second vertebral endplate contacting surfaces, wherein said first and second plate portions extend on said longitudinal axis and said medial and lateral visualization markers are located on opposite sides of said longitudinal axis and said medial marker being located distally of said lateral marker along said longitudinal axis so that a line extending between said medial and lateral markers is obliquely oriented to said longitudinal axis, wherein said medial and lateral markers are configured so that in a lateral image of the adjacent vertebrae said medial and lateral markers are aligned with one another so that only one of the medial and lateral markers is visible when said longitudinal axis is oriented along an oblique approach to the spinal disc space, wherein each of said first and second plate portions include a distal end and a proximally facing edge located proximally of said distal end of said respective plate portion, each of said edges extending from said respective plate portion toward the other of said first and second plate portions, said edges defining an entry into a space between said first and second plate portions with said first and second plate portions each including an inner surface extending along said space from said edge thereof to said distal end thereof and said actuating member includes an elongated shaft extending through said passage and an engaging member at a distal end of said shaft, and said actuating member and said engaging member are movable in said passage and said engaging member is structured to move past said edges into said space to contact said inner surfaces and provide incremental adjustment of said distraction height between said vertebral endplate contacting surfaces based on a position of said engaging member relative to said inner surfaces of said first and second plate portions.

10. The instrument of claim 9, wherein said inner surfaces of said first and second plate portions include a stepped configuration therealong, said stepped configuration including a distal portion providing a first distraction height when in contact with said engaging member, an intermediate portion providing a second distraction height when in contact with said engaging member, and a proximal portion providing a third distraction height when in contact with said engaging member.

11. The instrument of claim 10, wherein said second distraction height is greater than said third distraction height and said first distraction height is greater than said second distraction height.

12. The instrument of claim 9, wherein said first and second plate portions each include a distal end wall obliquely oriented with said longitudinal axis across said longitudinal axis, said first and second plate portions each including a proximal end and opposite sides extending between said distal end wall and said proximal end, wherein one of said opposite sides is longer than the other of said opposite side from said proximal end to said distal end wall.

13. The instrument of claim 9, wherein said medial and lateral visualization markers each include a housing extending from said plate portion.

14. An instrument positionable in a spinal disc space for distracting adjacent vertebrae, comprising:
a first plate portion positionable along an endplate of one of the adjacent vertebrae;
a second plate portion positionable along an endplate of the other of the adjacent vertebrae, said first and second plate portions each including a shaft portion extending proximally therefrom along a longitudinal axis to a hinge connecting said shaft portions to one another, said first and second plate portions further including opposite vertebral endplate contacting surfaces defining a distraction height therebetween, wherein said first plate portion and said second plate portion extend distally from said shaft portion along said longitudinal axis:
a handle at a proximal end of said shaft portions, said handle and said shaft portions defining a longitudinal passage;
an actuating member positionable in said passage operable to separate said first and second plate portions to increase the distraction height to distract the adjacent vertebrae; and a medial visualization marker adjacent a medial side of said first and second plate portions and a lateral visualization marker adjacent a lateral side of said first and second plate portions each projecting from at least one said first and second vertebral endplate contacting surfaces, wherein said first and second plate portions extend on said longitudinal axis and said medial and lateral visualization markers are located on opposite sides of said longitudinal axis and said medial marker being located distally of said lateral marker along said longitudinal axis so that a line extending between said medial and lateral markers is obliquely oriented to said longitudinal axis, wherein said medial and lateral markers are configured so that in a lateral image of the adjacent vertebrae said medial and lateral markers are aligned with one another so that only one of the medial and lateral markers is visible when said longitudinal axis is oriented along an oblique approach to the spinal disc space, wherein said medial and lateral visualization markers each include a housing extending from said plate portion and each of said housings is plastic and each of said medial and lateral visualization markers is a metal ball captured in said housing.

* * * * *

UNITED STATES PATENT AND TRADEMARK OFFICE
CERTIFICATE OF CORRECTION

| | |
|---|---|
| PATENT NO. | : 7,875,034 B2 |
| APPLICATION NO. | : 11/375229 |
| DATED | : January 25, 2011 |
| INVENTOR(S) | : Josse et al. |

It is certified that error appears in the above-identified patent and that said Letters Patent is hereby corrected as shown below:

In Column 6, Line 4, delete "axus 71" and insert -- axis 71 --, therefor.

In Column 10, Line 47, in Claim 1, after "of said" delete "of said".

In Column 11, Line 48, in Claim 9, delete "plate to" and insert -- plate portions to --, therefor.

In Column 12, Line 58, in Claim 14, delete "axis:" and insert -- axis; --, therefor.

Signed and Sealed this
Nineteenth Day of April, 2011

David J. Kappos
*Director of the United States Patent and Trademark Office*